United States Patent [19]

Talley

[11] Patent Number: 4,533,768
[45] Date of Patent: Aug. 6, 1985

[54] ZINC OXIDE CATALYZED DEALKYLATION OF ALKYLATED PHENOLS

[75] Inventor: John J. Talley, Clifton Park, N.Y.

[73] Assignee: General Electric Company, Schenectady, N.Y.

[21] Appl. No.: 606,504

[22] Filed: May 3, 1984

[51] Int. Cl.³ .............................................. C07C 37/50
[52] U.S. Cl. ................................................... 568/805
[58] Field of Search ......................................... 568/805

[56] References Cited

U.S. PATENT DOCUMENTS

| | | | |
|---|---|---|---|
| 3,998,892 | 12/1976 | Leach | 568/805 |
| 4,060,560 | 11/1977 | Leach | 568/805 |
| 4,071,566 | 1/1978 | Leach | 568/805 |
| 4,110,253 | 8/1978 | Leach | 568/805 |
| 4,191,844 | 3/1980 | Bjornson | 568/805 |
| 4,230,895 | 10/1980 | Daly | 568/805 |
| 4,230,896 | 10/1980 | Daly | 568/805 |

FOREIGN PATENT DOCUMENTS

| | | | |
|---|---|---|---|
| 45-39525 | 12/1970 | Japan | 568/805 |
| 277394 | 9/1927 | United Kingdom | 568/805 |

OTHER PUBLICATIONS

Jelinek, "Chem. Abstracts", vol. 55 (1961), p. 7357.

*Primary Examiner*—Werren B. Lone
*Attorney, Agent, or Firm*—Richard J. Traverso; James C. Davis, Jr.; James Magee, Jr.

[57] ABSTRACT

Selective catalytic steam dealkylation of ortho- and para-positions of alkylated phenols is accomplished by reacting ortho- and/or para-alkylated phenols with steam in the presence of a catalyst comprised of zinc oxide, optionally manganese oxide and optionally an organic binder and preferably an oxidizing atmosphere. High degrees of conversion are obtained without loss of the hydroxyl group of the alkylated phenols.

20 Claims, No Drawings

ZINC OXIDE CATALYZED DEALKYLATION OF ALKYLATED PHENOLS

BACKGROUND OF THE INVENTION

This invention relates to a method for dealkylating alkyl phenols. More particularly, this invention is directed to a method for dealkylating ortho- and para-alkylated phenols with steam in the presence of a zinc oxide catalyst.

It is often desirable to dealkylate the alkylated phenols obtained from coal tars from coal liquifaction processes to provide more valuable products, such as phenol. In addition, it is often desirable to dealkylate 2,4,6-trimethylphenol (TMP), a coproduct in the synthesis of 2,6-xylenol, to more useful alkylated phenols and phenol. These include p-cresol, o-cresol, 2,5-xylenol, 2,4-xylenol and the like.

Methods of dealkylating alkylated phenols are known to the art. These methods include thermal dealkylation, thermal hydrodealkylation and catalytic hydrodealkylation. Thermal dealkylation involves exposing dealkylated phenols to high temperatures (about 800° C.) to achieve thermal cracking of the alkylated phenol and yield phenol. However, this process is not selective and a substantial amount of dehydroxylation occurs under these conditions, producing the less valuable benzene and alkyl-substituted benzene species, as is shown more particularly by Daly in Journal of Catalysis 61, 528 (1980), the contents of which are incorporated herein by reference.

Thermal hydrodealkylation of alkylated phenols involves exposing the alkylated phenols to high temperatures in the presence of steam or hydrogen or both, as is shown by Daly in U.S. Pat. No. 4,230,895. This process also causes a significant amount of dehydroxylation, which is undesirable since dehydroxylation produces less valuable products.

Catalytic hydrodealkyation is typically more selective than the processes described above and causes less dehydroxylation. Daly describes a process in U.S. Pat. No. 4,230,896 wherein alkylated phenols are reacted with steam in the presence of a catalyst comprised of a hydrous carrier, a deactivation suppressor and at least one promoter. Catalysts included within those described by Daly include platinum and palladium on alumina and mixtures of palladium and chromium oxide on alumina. A catalytic hydrodealkylation process which reacts alkylated phenols with hydrogen is described by Bjornson in U.S. Pat. No. 4,191,844. This reaction takes place in the presence of a catalyst consisting essentially of magnesium oxide and a Group IIA metal oxide such as manganese oxide. Although these catalytic hydrodealkylation processes are more selective and cause less dehydroxylation than thermal hydrodealkylation, there still remains room for improvement. For example, the percentage of alkylated phenol converted to a new material is very low (about 40%) in the process described in U.S. Pat. No. 4,230,896 and dehydroxylation is still significant providing 5-30 weight % dehydroxylated products. When the alkylated phenols are reacted with hydrogen in the process described by Bjornson, the rate of dehydroxylation is also high, producing large quantities of dehydroxylated products (up to 50 weight %) at high rates of dealkylation. In addition, these processes which utilize a catalyst to dealkylate alkylated phenols are handicapped by the short lifetime of the catalyst due to coking. The catalyst must be reactivated or regenerated periodically and a deactivation suppressant is often necessary.

The catalytic hydrodealkylation process comprising this invention utilizes a zinc oxide catalyst which provides high conversion rates with essentially no loss of hydroxy groups from dehydroxylation.

SUMMARY OF THE INVENTION

A method of dealkylating ortho-alkylated and para-alkylated phenols with substantially no dehydroxylation is provided comprising reacting an alkylated phenol with steam in the presence of a catalyst comprising zinc oxide, said alkylated phenols having at least one alkyl radical of from 1 to 6 carbon atoms either ortho-positioned or para-positioned to the hydroxyl radical. The reaction preferably takes place in the presence of air to extend the catalyst life.

OBJECTS OF THE INVENTION

An object of the invention is to dealkylate alkylated phenols with substantially no loss of hydroxyl radicals.

Another object of the present invention is to dealkylate alkylated phenols at a high conversion rate without loss of selectivity.

Another object of the present invention is to provide a new catalyst for dealkylating alkylated phenols by a catalytic steam dealkylation process.

DETAILED DESCRIPTION OF THE PREFERRED EMBODIMENT

The present invention is directed to a catalytic steam dealkylation process which selectively dealkylates the ortho- and para-positions with respect to the hydroxyl radical of an alkylated phenol. The term "dealkylation" as used herein refers to the removal of alkyl groups containing 1 to 6 carbon atoms from the aromatic nucleus of phenols. The term "dehydroxylation", as used herein, refers to the loss of the hydroxyl radical on the aromatic nucleus of the alkylated phenols. The process comprising this invention dealkylates alkylated phenols with essentially no dehydroxylation.

Suitable alkylated phenols which can be dealkylated by this process include those containing one hydroxyl radical and at least one alkyl group at an ortho or para-position relative to said hydroxyl radical. These alkylated phenols may contain multiple alkyl groups at multiple positions on the aromatic nucleus and these alkyl groups may be straight or branch chained. Examples of suitable alkylated phenols include ortho-cresol, para-cresol and isomers of xylenol, ethyl phenol, n-propylphenol, etc.; which contain at least one alkyl substituent on a para- or ortho-position with respect to the hydroxyl radical. More particularly these include ortho-cresol, para-cresol, 2,4-xylenol, 2,3-xylenol, 2,5-xylenol, 2,6-xylenol, 2,3,4-trimethylphenol, 2,3,5-trimethylphenol, 2,3,6-trimethylphenol, 2,4,6-trimethylphenol, 2,4,5-trimethylphenol, 3,4,5-trimethylphenol, 2-ethylphenol, 4-ethylphenol, 2,4-diethylphenol, 2-isopropyl phenol, etc. The feed of alkylated phenols may be comprised of one single alkylated phenol or a mixture of alkylated phenols; mixtures typically being derived from tar acids obtained from coal liquifaction processes.

The alkylated phenols of the reactor feed may be dissolved in an organic solvent so as to make addition into the reactor easier. Any organic solvent which is inert under dealkylation conditions is suitable, provided it is a good solvent medium for the alkylated phenols.

The preferred solvent is benzene. Other suitable solvents include tetrahydrofuran, chlorobenzene, hexane, etc.

The reactor feed also contains steam, either saturated, unsaturated or superheated. The molar ratio of steam to alkylated phenol may be at any value and still provide dealkylation; but preferably, the molar ratio of steam/alkylated phenol falls within the range of about 0.5:1 to about 100:1. The most preferred range of molar ratios for steam/alkylated phenol falls within the range of about 1:1 to 5:1.

The reaction between the alkylated phenol and steam takes place in the presence of a catalyst comprised of zinc oxide. Any catalytic form of zinc oxide is suitable for use in this process. It is preferable that the zinc oxide within said catalyst fall within the range of about 80–90% by weight and that said catalyst be free of oxide compounds which tend to be acidic in nature; such as aluminum oxide, silicon dioxide, silica-alumina, acidic clays, etc. However, small quantities of these materials can be tolerated if they are fired to a temperature where they become inert. As such, they may be used as a support for the zinc oxide without detrimental effect. Oxides of metals which are basic in nature, as is zinc oxide, may be present in minor proportions without a significant detrimental effect to the activity of zinc oxide. Many "basic oxides", when used alone, do not have the reactivity or selectivity which zinc oxide catalysts exhibit and do not provide significant benefits. Examples of such "basic oxides" include, manganese oxide, magnesium oxide and lead oxide. If utilized, they are preferably not present in an excess of 10 weight % of the total catalyst.

These zinc oxide catalysts may have an inert organic or inorganic binder mixed within in order to permit them to be pelletized and easily handled in the process. Such binders may preferably comprise up to about 20 weight % of said catalyst. Suitable organic binders include: polyphenylene oxide, graphite, etc. Silica is an example of a suitable inorganic binder. Polyphenylene oxide binders are the most preferred.

A suitably porous zinc oxide catalytic material may be obtained by oxidation (burning) of zinc metal or zinc ore. If desired, the zinc metal or ore can be coated on an inert carrier or binder, pelletized and then oxidized to give a porous zinc oxide coating on the inert substrate. The zinc metal or ore may be oxidized prior to placement within the reactor or this may be accomplished within the reactor. It is preferable to oxidize the material at about 300° to 500° C. under an oxidation atmosphere such as oxygen gas, air, etc.

Zinc oxide catalysts retain their activity only for a short period of time. Carbon deposition (coking) quickly decreases the activity of the zinc oxide catalysts (about 2 hours). When this occurs, the zinc oxide catalysts can be regenerated by oxidation of the carbon by passing oxygen or air over the catalyst at temperatures in the range of about 400° to 500° C.

An alternative method utilized to retard the coking of the zinc oxide catalyst surface is to introduce an oxidizing atmosphere (oxygen or air) into the reactor via the reactor feed so that the reaction takes place in the presence of this oxidizing atmosphere, which is preferably air. The preferred volume (flow rate) of oxidizing atmosphere which performs this function provides a value for the mole/hr. ratio of oxygen ($O_2$) to alkylated phenol in the range of about 1 to 50. The most preferred values for this ratio fall within the range of 1 to 5.

Smaller and larger quantities of oxidizing atmosphere are also effective and do not inhibit the process from achieving its desired objects and do not cause dehydroxylation. The catalyst may have to be regenerated if smaller quantities are used.

The dealkylation reaction proceeds at a temperature within the range of from about 400° to 675° C. with substantially no dehydroxylation, with temperatures within the range of 450° to 550° C. being preferred and about 500° C. being most preferred. These preferred temperature ranges can vary if the reaction takes place at a pressure other than at 1 atmosphere. At such temperatures, the alkylated phenols in the feed and the dealkylated phenols produced are in vapor form. The reaction proceeds smoothly at atmospheric pressure, which makes it convenient to carry out the process since complex equipment is not required and the hazards which are characteristic of reactions which proceed under pressure avoided. However, pressures above and below. atmospheric pressure can be utilized when desired. The pressure is preferably maintained within the range of about 1 to 50 atmospheres, with pressure at about 1 atmosphere being the most preferred.

The rate at which alkylated phenols are fed into the reactor to react with steam in the presence of catalyst (liquid hourly space velocity) is not critical to achieve the desired objects of this invention. The flow rate of reactant does effect the product yield by determining the amount of contact time between the alkylated phenols, steam and catalyst. Due to the difference in the specific activities of zinc oxide catalysts, each catalyst will have a different optimum flow rate than another. The more active the catalyst, the shorter contact time necessary to produce the same quantity of dealkylated phenols. Therefore, to obtain a particular conversion rate, higher liquid hourly space velocities can be used with more active catalysts while lower liquid hourly space velocities are necessary with less active catalysts. A flow rate which is too high will flood the catalyst and not permit the reaction to proceed. A flow rate having a liquid hourly space velocity in the range of about 0.1 to 3.0 grams alkylated phenol/hour/grams of catalyst is preferred. The most preferred flow rate is at a liquid hourly space velocity of about 0.3 to 0.5 grams of alkylated phenol/hour/grams of catalyst.

The starting materials are preferably in the vapor phase when in the presence of the zinc oxide catalyst at the operable temperature ranges. To avoid cooling of the catalyst below the reaction temperature selected, it is preferable to vaporize and preheat the starting materials prior to contact with the zinc oxide catalyst. To minimize the decomposition of the starting materials, the starting materials are maintained at the minimum temperature necessary to provide vaporization and they are then preheated to the reaction temperature immediately prior to contact with the zinc oxide catalyst. This can be accomplished by passing the vaporized starting materials through a heated tube of metal or quarts or by passing the vaporized starting materials over heated quartz beads just prior to entry into the catalyst bed. It is preferable to utilize the same heating medium to preheat the vapors which is used to heat the catalyst bed so as to maintain a stable reaction temperature within the reactor.

Both products and unreacted starting materials exit the zinc oxide catalyst bed preferably in vapor form and are typically condensed to a liquid for subsequent use.

This can be accomplished by any conventional means, such as common air or water condenser. The products are then separated from the condenser effluent, preferably by distillation in a conventional distillation apparatus.

The process can be carried out in a conventional reactor used for vapor phase reactions over a solid catalyst. For example, a tubular reactor of quartz or metal filled with a static bed of zinc oxide catalyst is suitable. The reactor is heated to the desired temperature by any conventional means; for example, it can be heated by surrounding the reactor with an electric heater or by surrounding the reactor with a heated gas or liquid. Multiple electric heaters with separate controls permit the catalyst bed temperature to be controlled quite easily, even though the reaction is exothermic.

In order that those skilled in the art may better understand this invention, the following experiments are provided by way of explanation and not by way of limitation.

EXPERIMENTAL

In each of Examples 1 through 23, the following procedure was utilized.

An electrically heated 1 inch by 12 inch quartz tubular reactor was wrapped with three heating tapes and three thermocouples at 6 inch intervals to monitor the temperature along the catalyst bed. The three heating tapes were controlled by three variable transformers such that the temperature of the catalyst bed was controlled to within ±10° C. The quartz tube was packed with 5 ml quartz beads followed by 100 ml of zinc oxide catalyst. The last three to four inches of the reactor were packed with quartz beads. The catalyst was oxidized at about 450° to 500° C. for three to four hours under a flow of air (0.1 SCFH). The catalyst bed was then brought to the desired temperature. The reactants were introduced at the top of the bed with a metering pump (Eldex Laboratories Model AA-72-S) at a rate which provided a liquid hourly space velocity of about 0.5, unless indicated otherwise. An airflow was maintained throughout all experiments, unless otherwise indicated, at a flow rate between about 0.005 to 0.8 standard cubic feet per hour (SCFH). The products which exited the reactor were condensed and the organic effluent was separated from the water and analyzed by gas chromatography with a Varian Associates Vista 6000 chromatograph.

EXAMPLES 1-6

In Examples 1-6 the feedstock comprised 2,4-xylenol, air and steam, which was passed over a zinc oxide catalyst for one hour. The flow of air was maintained at 0.05 standard cubic feet hour (SCFH) and the flow of 2,4-xylenol and steam were each maintained at a flow rate of 0.25 liquid hourly space velocity (LHSV). The temperature of the catalyst bed varied for each example and is indicated in Table I along with the products obtained. No dehydroxylated products were observed.

TABLE I

| Example | T (°C.) | P | OC | PC | 2,6 | 2,4 | 2,4,6 |
|---|---|---|---|---|---|---|---|
| 1 | 550 | 8.35 | 1.12 | 44.29 | 0.48 | 43.14 | 1.63 |
| 2 | 400 | 0.09 | 0.50 | 6.34 | 0.00 | 79.80 | 10.35 |
| 3 | 400 | 0.20 | 0.33 | 10.04 | 0.00 | 85.25 | 3.65 |
| 4 | 420 | 0.74 | 1.05 | 18.62 | 0.00 | 68.16 | 10.64 |

TABLE I-continued

| Example | T (°C.) | P | OC | PC | 2,6 | 2,4 | 2,4,6 |
|---|---|---|---|---|---|---|---|
| 5 | 500 | 14.04 | 1.07 | 73.38 | 0.00 | 9.36 | 1.18 |
| 6 | 555 | 12.78 | 1.24 | 55.65 | 0.00 | 28.59 | 1.74 |

P = phenol; OC = o-cresol; PC = p-cresol; 2,6 = 2,6-xylenol; 2,4 = 2,4-xylenol; 2,4,6 = 2,4,6-trimethylphenol.

EXAMPLE 7

In Example 7 six runs were made with a feedstock comprised of 2,4-xylenol, air and steam at the same reaction temperature of 500° C. by passing the feedstock over a ZnO catalyst for 1 hour. The flow rate of air was maintained at 0.05 SCFH and the flow rates of 2,4-xylenol and steam were each maintained at 0.25 LHSV. The products obtained are provided in Table II. No dehydroxylated products were obtained.

TABLE II

| Run | P | OC | PC | 2,6 | 2,4 | 2,4,6 |
|---|---|---|---|---|---|---|
| 1 | 4.24 | 1.27 | 47.01 | 0.00 | 42.27 | 4.57 |
| 2 | 14.55 | 1.21 | 72.80 | 6.00 | 9.45 | 1.40 |
| 3 | 14.50 | 1.39 | 71.14 | 0.00 | 10.69 | 1.65 |
| 4 | 14.71 | 1.21 | 72.38 | 0.00 | 9.70 | 1.44 |
| 5 | 9.78 | 1.12 | 70.23 | 0.00 | 17.67 | 1.20 |
| 6 | 7.71 | 1.22 | 70.96 | 0.00 | 18.90 | 1.21 |

P = phenol; OC = o-cresol; PC = p-cresol; 2,6 = 2,6-xylenol; 2,4 = 2,4-xylenol; 2,4,6 = trimethylphenol.

EXAMPLES 8-9

In Example 8, two runs were made over a ZnO catalyst with a feedstock comprised of 2,4,6-trimethylphenol (20 g) dissolved in benzene (30 g), air and steam. For Example 9, the feedstock comprised 2,4,6-trimethylphenol (without the benzene), air and steam. The flow of air was maintained at 0.05 SCFH and the temperature was maintained at 500° C. in both examples. The flow of steam and the 2,4,6-trimethylphenol solution were both 0.25 LHSV and for Example 9 the flow of steam and 2,4,6-trimethylphenol were both 0.50 LHSV. The products obtained for both examples are shown in Table III. No dehydroxylated products were observed.

TABLE III

| Example | Run | P | OC | PC | 2,6 | 2,4 | 2,4,6 |
|---|---|---|---|---|---|---|---|
| 8 | 1 | 37.52 | 1.45 | 51.14 | 0.43 | 5.63 | 3.38 |
| 8 | 2 | 37.04 | 1.28 | 50.74 | 0.00 | 5.34 | 3.26 |
| 9 | — | 3.95 | 1.86 | 35.14 | 1.21 | 24.30 | 32.61 |

P = phenol; OC = o-cresol; PC = p-cresol; 2,6 = 2,6-xylenol; 2,4 = 2,4-xylenol; 2,4,6 = 2,4,6-trimethylphenol.

EXAMPLE 10

A feedstock comprised of p-cresol, air and steam was passed over a ZnO catalyst for 1 hour. The reaction temperature was maintained at about 500° C., the air flow was maintained at 0.05 SCFH and the flow of p-cresol and steam were both maintained at 0.25 LHSV. The products obtained were as follows: 11.86 weight % phenol and 88.14 weight % p-cresol. No other products were observed.

EXAMPLE 11

A feedstock comprised of 2,6-xylenol (0.25 LHSV), air (0.05 SCFH) and steam (0.25 LHSV) was passed over a ZnO catalyst for 1 hour in accordance with the procedure described above. The temperature was maintained at about 500° C. and the following products were provided: 51.41 weight % phenol, 26.30 weight % o-cresol, 6.00 weight % p-cresol, 22.29 weight % 2,6-xylenol and no 2,4,6-trimethylphenol, 2,4-xylenol or dehydroxylated products.

EXAMPLES 12–18

For Examples 11–16 feedstocks comprised of 2,4-xylenol, steam and air (0.05 SCFH) were passed over a ZnO catalyst for 1 hour in accordance with the procedure described above. The temperature for each example was maintained at about 500° C. The flow rates of 2,4-xylenol and steam varies in each example. The flow rates utilized and products obtained are indicated in Table IV. No dehydroxylated products were observed.

TABLE IV

| Example | P | OC | PC | 2,6 | 2,4 | 2,4,6 | 2,4-xylenol (LHSV) | H₂O (LHSV) |
|---|---|---|---|---|---|---|---|---|
| 12 | 6.51 | 0.85 | 72.07 | 0.00 | 17.54 | 2.70 | 0.26 | 0.26 |
| 13 | 1.72 | 1.06 | 54.50 | 6.00 | 35.73 | 6.99 | 0.45 | 0.23 |
| 14 | 6.83 | 1.04 | 69.12 | 0.00 | 21.17 | 1.84 | 0.23 | 0.45 |
| 15 | 0.00 | 0.64 | 13.04 | 0.00 | 81.10 | 5.22 | 0.45 | 0.00 |
| 16 | 6.14 | 1.02 | 65.85 | 0.00 | 24.01 | 2.98 | 0.45 | 0.28 |
| 17 | 7.65 | 1.01 | 70.89 | 0.00 | 18.27 | 2.18 | 0.22 | 0.22 |
| 18 | 5.91 | 0.73 | 65.75 | 0.00 | 25.37 | 2.24 | 0.22 | 0.22 |

P = phenol; OC = o-cresol; PC = p-cresol; 2,6 = 2,6-xylenol; 2,4 = 2,4-xylenol; 2,4,6 = 2,4,6-trimethylphenol.

EXAMPLES 19–24

In Examples 19–24, the feedstock comprised a mixture of alkylated phenols, steam and air (0.05 SCFH). The feedstock was passed over a ZnO catalyst at 500° C. in each example as described in the above procedure. The flow rates of the alkylated phenol mixture and steam for Examples 18–21 were both 0.13 LHSV and the flow rates for the mixture and steam were both 0.26 LHSV in Examples 22 and 23. The alkylated phenols in the feedstock and the products obtained for each example are given in Table V. No dehydroxylated products were observed.

TABLE V

| Ex. | Feedstock (wt. %) | P | OC | PC | 2,6 | 2,4 | 2,4,6 TMP |
|---|---|---|---|---|---|---|---|
| 19 | 2,4 xylenol(63)/2,4,6 TMP(37) | 9.01 | 1.61 | 64.18 | 0.00 | 19.11 | 6.09 |
| 20 | 2,4 xylenol(56)/2,4,6 TMP(44) | 9.91 | 1.59 | 64.20 | 0.00 | 18.16 | 5.72 |
| 21 | 2,4 xylenol(45)/2,4,6 TMP(55) | 15.37 | 1.15 | 69.02 | 0.00 | 10.62 | 3.85 |
| 22 | o-cresol(63)/2,4,6 TMP(27) | 63.17 | 5.42 | 27.91 | 0.00 | 2.22 | 1.29 |
| 23 | 2,4 xylenol(56)/2,4,6 TMP(44) | 2.50 | 1.14 | 50.57 | 0.00 | 25.93 | 14.03 |
| 24 | p-cresol(46)/2,4,6 TMP(54) | 55.79 | 7.10 | 20.75 | 0.00 | 7.23 | 9.13 |

P = phenol; OC = o-cresol; PC = p-cresol; 2,6 = 2,6-xylenol; 2,4 = 2,4-xylenol; TMP = trimethylphenol.

EXAMPLE 25

This example illustrates the ortho-para selectivity of the ZnO catalyst. A feedstock comprised of 10 ml m-cresol and 10 ml steam was passed over a ZnO catalyst at a temperature of about 550° C. The flow rate for both steam and m-cresol was about 0.2 ml/minute. Analysis of the condensate from this reaction showed that m-cresol is completely stable under these reaction conditions.

Although the above Examples have shown various modifications of the present invention, further modifications are possible in light of the above techniques by one skilled in the art without departing from the scope and spirit of this invention.

What is claimed is:

1. A method of removing one or more alkyl groups containing 1–6 carbon atoms from the aromatic nucleus of alkylated phenols that are ortho-positioned or para-positioned with respect to the hydroxy group with substantially no dehydroxylation comprising reacting an alkylated phenol with steam in the presence of a catalyst comprising zinc oxide and an oxidizing atmosphere at a temperature in the range of about 400° to 675° C., said alkylated phenols having at least one alkyl radical of from 1 to 6 carbon atoms either ortho-positioned or para-positioned to the hydroxyl radical.

2. A process as in claim 1 wherein the oxidizing atmosphere is selected from the group consisting of air and oxygen.

3. A process as in claim 1 wherein the flow rate of alkylated phenols is within the range of 0.1 to 1.0 grams/minute/gram of catalyst.

4. A method as in claim 1 wherein the weight ratio of alkylated phenol to steam is in the range of about 1:1 to 1:15.

5. A method as in claim 1 wherein the reaction takes place under a pressure within the range of about 1 to 50 atmospheres.

6. A method as in claim 1 wherein the catalyst is comprised of 80–90 weight % zinc oxide and about 1 to 20 weight % of an organic binder.

7. A process as in claim 6 wherein the organic binder is polyphenylene oxide.

8. A process as in claim 6 wherein said catalyst is in the presence of air during the reaction of alkylated phenol and steam.

9. A process as in claim 8 wherein the quantity of air utilized provides a value for the ratio of moles oxygen/hour:moles alkylated phenol/hour within the range of 1 to 5.

10. A process as in claim 6 wherein the ratio of steam to alkylated phenols is within the range of 1:1 to 15:1.

11. A process as in claim 6 wherein the temperature is maintained within the range of about 450° to 550° C. and the pressure is maintained at about 1 atmosphere.

12. A process as in claim 6 wherein the flow rate of alkylated phenols is within the range of about 0.1 to 1.0 grams/hour/gram of catalyst.

13. A process as in claim 1 wherein the alkylated phenols are selected from the group consisting of o-cresol, p-cresol, 2,4-xylenol, 2,6-xylenol, 2,5-xylenol, 2,3-xylenol, 3,4-xylenol, 2,4,6-trimethylphenol, 2,3,5-trimethylphenol, 2,3,6-trimethylphenol, 2-isopropylphenol, 2,3,4-trimethylphenol and 3,4,5-trimethylphenol.

14. A process as in claim 1 wherein the alkylated phenols are dissolved in an inert organic solvent.

15. A process as in claim 14 wherein the inert organic solvent is benzene.

16. A method of dealkylating alkylated phenols selected from the group consisting of 2,4-xylenol, 2,6-xylenol, 2,4,6-trimethylphenol, o-cresol and p-cresol; said method comprising reacting one or more of said alkylated phenols with steam in the presence of a catalyst comprising 80–98 wt. % zinc oxide and 1 to 20 weight % polyphenylene oxide in the presence of air at a temperature in the range of about 450° to 550° C., the ratio of alkylated phenol to steam falling within the range of about 1:0.5 to 1:5.

17. A method as in claim 16 wherein the flow rate of reactants falls within the range of about 0.1 to 1.0 grams/hour/gram of catalyst and the volume of air provides a value for the ratio moles oxygen/hour:moles alkylated phenols/hour in the range of 1 to 5.

18. A process as in claim 16 wherein the organic binder is polyphenylene oxide.

19. A method of dealkylating 2,4,6-trimethylphenol wherein 2,4,6-trimethylphenol is reacted with steam in the presence of a catalyst compound of 80–98 weight % zinc oxide, and 1 to 20 weight % of a polyphenylene oxide organic binder, said flow rate of 2,4,6-trimethylphenol flowing within the range of about 0.1 to 1.5 grams/hour/gram of catalyst, said ratio of steam to phenol falling within the range of about 0.5:1 to 15:1, said volume of air providing a value for the ratio moles oxygen/hour:moles alkylated phenol/hour in the range of 1 to 5, said temperature range falling within the range of about 500° to 550° C. and said pressure being at about 1 atmosphere.

20. A method of dealkylating 2,4-xylenol wherein 2,4-xylenol is reacted with steam in the presence of a catalyst comprised of 80–98 weight % zinc oxide and 1 to 20 weight % of a polyphenylene oxide organic binder, said flow rate of 2,4-xylenol falling within the range of about 0.1 to 1.0 grams/hour/gram of catalyst, said phenol to steam ratio falling within the range of about 0.5:1 to 1:15, said volume of air providing a valve for the ratio moles Oxygen/hour:moles alkylated phenol/hour in the range of 1 to 5, said temperature falling within the range of about 500 to 550° C. and said pressure being at about 1 atmosphere.

* * * * *